US00PP27915P3

(12) United States Plant Patent
Van Dijk

(10) Patent No.: US PP27,915 P3
(45) Date of Patent: Apr. 18, 2017

(54) *ANTHURIUM* PLANT NAMED 'ANTHEPDAK'

(50) Latin Name: *Anthurium andreanum L.*
Varietal Denomination: ANTHEPDAK

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 60 days.

(21) Appl. No.: 14/545,589

(22) Filed: May 27, 2015

(65) Prior Publication Data

US 2016/0353645 P1 Dec. 1, 2016

(51) Int. Cl.
*A01H 5/02* (2006.01)

(52) U.S. Cl.
USPC ..... Plt./365

(58) Field of Classification Search
USPC ..... Plt./365, 367, 369
See application file for complete search history.

(56) References Cited

U.S. PATENT DOCUMENTS

PP22,629 P2 * 4/2012 van Dijk ..... Plt./365

OTHER PUBLICATIONS

New Plants and Flowers. Four new pot *Anthuriums* Jun. 3, 2014, retrieved on Sep. 14, 2016, retrieved from the Internet at <http://www.newplantsandflowers.com/four-new-pot-anthuriums/> 2 pp.*
Upov Pluto Plant Variety Database Sep. 14, 2016 for *Anthurium* Anthepdak, retrieved on Sep. 14, 2016, retrieved from the Internet at <https://www3.wipo.int/pluto/user/en/index.jsp> one page.*
EU Community Plant Variety Rights Application No. 2013/1866, Application No. A201300736, filed Jul. 5, 2013, 7 pages.
EU Community Plant Variety Office Official Gazette, May 2013, Oct. 15, 2013, cover page and pp. 29, 48.
www.newplantandflowers.com/four-new-pot-anthuriums/, published Jun. 3, 2014, 2 pages, retrieved from the internet on Dec. 7, 2016.
Anthura *Anthurium*: Cut flower and pot plant culture, published Nov. 2014, cover page and pp. 39, 47.
EU Community Plant Variety Rights Grant No. EU 41014, issued May 26, 2015, 2 pages.
Anthura *Anthurium* catalogue: Cut flower and pot plant 2015/2016, published May 2015, cover page and pp. 46, 55, 58.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHEPDAK' particularly distinguished by having large, pink, very durable spathes that retain the original color for a long period of time, dark green, durable and glossy leaves, flowering continuously throughout the year and a plant height of 50 cm to 55 cm, is disclosed.

3 Drawing Sheets

Genus and species: *Anthurium andreanum* L.
Variety denomination: 'ANTHEPDAK'.

BACKGROUND OF THE NEW PLANT

The present invention comprises a new and distinct variety of *Anthurium*, botanically known as *Anthurium andreanum* L., and hereinafter referred to by the variety name 'ANTHEPDAK'. The new variety originated from a hybridization made in October 2007 in Bleiswijk, The Netherlands. The female parent is a red *Anthurium* pot plant designated '5432-12' (unpatented), and the male parent was a red *Anthurium* plant designated '7095-01' (unpatented).

A single plant was selected in October 2009 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Jul. 5, 2013, in Japan on Jun. 2, 2014, in China on Jan. 29, 2015 and in Vietnam on Mar. 23, 2015. 'ANTHEPDAK' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Big, shiny, pink, cordate spathe;
2) White spadix with yellow tip;
3) Compact plant habit; and
4) Shiny, dark green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 40-week old plant grown in a greenhouse in Bleiswijk, The Netherlands in April 2015.

Figure 1:
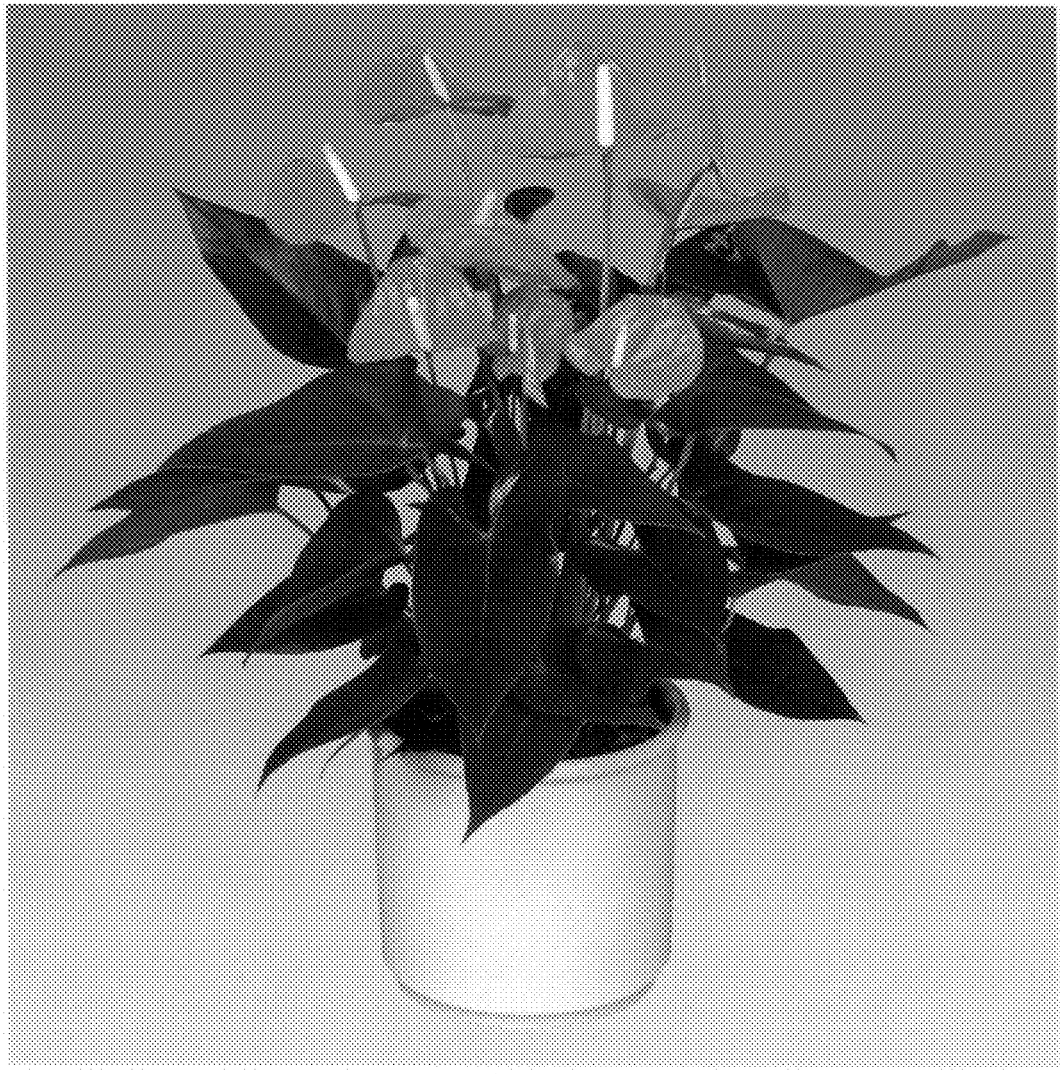
Figure 2:
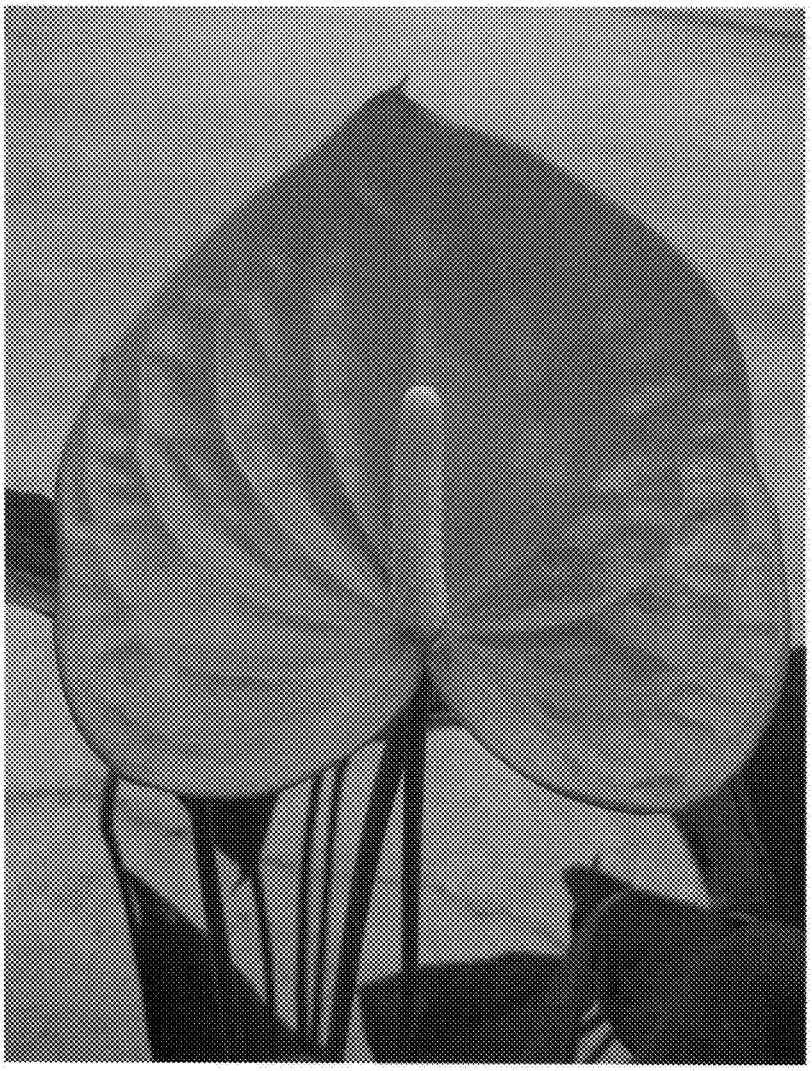
Figure 3:
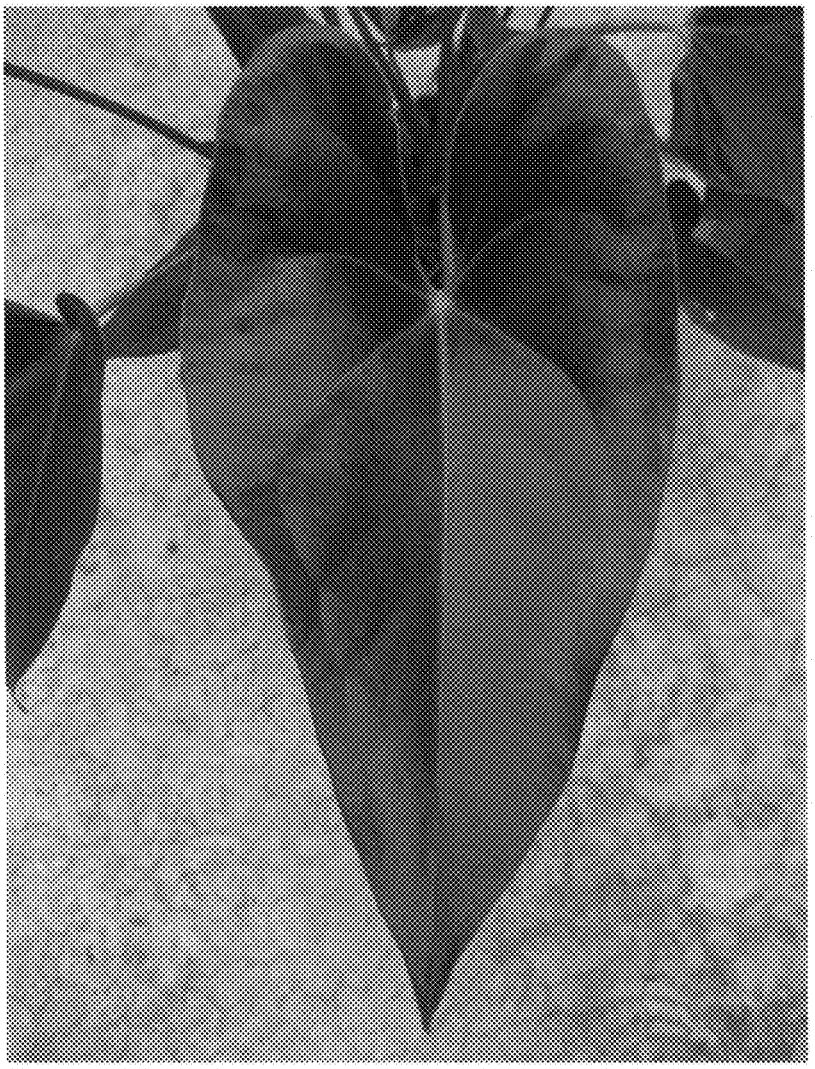

FIG. 1 shows the overall plant habit.
FIG. 2 shows a close-up of the mature spathe.
FIG. 3 shows the upper leaf blade surface.

DESCRIPTION OF THE NEW VARIETY

The following detailed description sets forth the distinctive characteristics of 'ANTHEPDAK'. The data which define these characteristics were collected from asexual reproductions carried out in Bleiswijk, The Netherlands. The plant history was taken on 40-week old plants which were planted from tissue culture in 17-centimeter pots and grown in a glass greenhouse between 19° C. and 24° C. Observations were made in April 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHEPDAK'.

Parentage:

*Female parent*.—*Anthurium* plant '5432-12' (unpatented).

*Male parent*.—*Anthurium* plant '7095-01' (unpatented).

Plant:

*Propagation*.—Tissue culture.

*Root description*.—Fleshy white-cream colored roots with small hairy lateral roots having yellow-colored root tips.

*Time to produce a finished flowering plant*.—35 to 40 weeks for a 17 cm pot.

*Growth habit*.—Herbaceous perennial.

*Height* (*measured from soil, including inflorescence*) .—50.0 cm to 55.0 cm.

*Width* (*measured from leaf tips*).—50.0 cm to 60.0 cm.

Leaves:

*Immature leaves*.—Length: 8.0 cm to 12.0 cm. Width: 5.0 cm to 7.0 cm. Color: Upper surface: RHS 146A. Lower surface: RHS 144A. Texture (both upper and lower surfaces): Shiny.

*Mature leaves*.—Length (fully expanded): 18.0 cm to 23.0 cm. Width: 10.0 cm to 14.0 cm. Shape: Long cordate. Apex: Acuminate. Base: Cordate. Leaf blade angle with the petiole: Between 120 degrees and 140 degrees. Leaf margin: Entire. Color: Upper surface: RHS 147A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Arrangement: Leaf blade has two lobes extending past the petiole. The lobes are non-touching. Length of lobes of mature leaf blades: 4.0 cm to 6.0 cm. Width of lobes of mature leaf blades: 3.0 cm to 5.0 cm. Distance from petiole/leaf junction to highest point on lobes of mature leaf blades: 3.0 cm to 6.0 cm.

*Petiole*.—Cross-section: Round. Diameter: 0.3 cm to 0.4 cm. Length: 16.0 cm to 20.0 cm for a mature leaf size. Color: Mature leaf: RHS 144A. Immature leaf: RHS 144A. Cataphyll color surrounding the petiole: Outside: RHS 152A. Inside: RHS 199D.

*Geniculum*.—Length: 1.5 cm to 2.5 cm. Width: 0.35 cm to 0.45 cm. Color: RHS 144B.

Inflorescence:

*Arrangement*.—Single.

*Flowering habit* (*length of flowering season*).—Continuous.

*Number of inflorescences per plant*.—4 to 6.

*Fragrance*.—Absent.

*Longevity of inflorescence on plant*.—Over a year.

*Longevity of the flower as a cut flower*.—35 to 45 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 90 degrees and 120 degrees; the spathe stands on a wiry peduncle about 3.0 cm to 6.0 cm above the foliage.

*Shape*.—Cordate.

*Apex*.—Broad acuminate.

*Base*.—Cordate.

*Texture*.—Shiny and slightly blistered.

*Margin*.—Entire.

*Lobe position*.—Free.

*Size*.—Height: 30.0 cm to 40.0 cm (peduncle length at maturity). Length: 9.0 cm to 12.0 cm. Width: 9.0 cm to 12.0 cm.

*Color*.—Just fully open: Upper surface: RHS 52A. Lower surface: RHS 52B.

Peduncle:

*Shape*.—Erect.

*Cross-section*.—Round.

*Length*.—30.0 cm to 40.0 cm.

*Diameter*.—0.3 cm to 0.4 cm.

*Color*.—RHS 144A.

Flowering time:

*General*.—One small rooted untreated tissue culture plant of 2.0 cm tall will flower after 9 to 10 months, depending on the season, and 3 to 4 blossoms will appear. More blossoms appear after some additional weeks so that a full flowering and commercial plant will have 6 to 8 pink spathes. Smaller blossoms may occur on less mature plants.

Spadix:

*Size*.—Length: 4.0 cm to 5.0 cm (depending on flower size). Width (at apex): 0.5 cm to 0.6 cm. Width (at base): 0.6 cm to 0.8 cm.

*Shape*.—Columnar.

*Angle from spadix tip to peduncle*.—150 to 180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 13B. Mature: RHS 158D.

Flowers:

*Quantity per spadix*.—180 to 240.

*Spadix flower arrangement*.—Bisexual, rounded in cross-section.

*Shape*.—Rounded.

*Size*.—Length: 0.05 cm to 0.1 cm. Diameter (maximum): 0.1 cm.
*Color*.—RHS 158B.
Reproductive organs:
*Stamens*.—Not visible.
*Pollen amount*.—Very few.
*Pollen color*.—RHS 155D.
*Pistil*.—Quantity: Many. Length: Less than 0.01 cm. Color: RHS 158B.
*Style*.—Not observed.
*Stigma*.—Shape: Ovoid. Diameter: Less than 0.01 cm. Color: RHS 158B.
*Ovary*.—Rarely visible.
*Ovary color*.—Not measured.
Fruit and seed set: None observed.
Disease and pest resistance: Not observed to date.

COMPARISON WITH PARENTAL AND COMMERCIAL VARIETIES

'ANTHEPDAK' differs from the female parent plant '5432-12' (unpatented) in that 'ANTHEPDAK' has a pink spathe, whereas '5432-12' has a red spathe.

'ANTHEPDAK' differs from male parent plant '7095-01' (unpatented) in that 'ANTHEPDAK' has a pink spathe, whereas '7095-01' has a red spathe.

'ANTHEPDAK' differs from commercial variety 'ANTHEPCI' (unpatented) in that 'ANTHEPDAK' has a long cordate leaf shape and dark pink spathe, whereas 'ANTHEPCI' has a broad cordate leaf shape and a light pink spathe. Additionally, 'ANTHEPDAK' has a larger spathe diameter than 'ANTHEPCI'.

'ANTHEPDAK' differs from commercial variety 'ANTHCASZIM' (U.S. Plant Pat. No. 22,629) in that 'ANTHEPDAK' has a long cordate leaf shape, whereas 'ANTHCASZIM' has a broad cordate leaf shape. Additionally, 'ANTHEPDAK' has a larger spathe diameter than 'ANTHCASZIM'.

I claim:

1. A new and distinct variety of *Anthurium* plant named 'ANTHEPDAK', substantially as illustrated and described herein.

* * * * *